US008196750B2

(12) United States Patent
Kanel et al.

(10) Patent No.: US 8,196,750 B2
(45) Date of Patent: Jun. 12, 2012

(54) PROCESS AND APPARATUS FOR ADSORPTIVE BUBBLE SEPARATION USING A DENSE FOAM

(75) Inventors: Jeffrey S. Kanel, Kingsport, TN (US); Robert L. Clayton, Tucson, AZ (US)

(73) Assignees: Renewable Algal Energy, LLC, Kingsport, TN (US); Eastman Chemical Company, Kingsport, TN (US)

( * ) Notice: Subject to any disclaimer, the term of this patent is extended or adjusted under 35 U.S.C. 154(b) by 163 days.

(21) Appl. No.: 12/665,227

(22) PCT Filed: Jun. 18, 2008

(86) PCT No.: PCT/US2008/007708
§ 371 (c)(1),
(2), (4) Date: Dec. 17, 2009

(87) PCT Pub. No.: WO2008/156835
PCT Pub. Date: Dec. 24, 2008

(65) Prior Publication Data
US 2010/0176062 A1 Jul. 15, 2010

Related U.S. Application Data

(60) Provisional application No. 60/944,813, filed on Jun. 19, 2007.

(51) Int. Cl.
*B03D 1/14* (2006.01)
*B03D 1/24* (2006.01)
*C02F 1/24* (2006.01)
*A01G 7/00* (2006.01)

(52) U.S. Cl. ..... 209/164; 209/170; 210/703; 210/221.2; 47/1.4

(58) Field of Classification Search .................. 210/703, 210/221.2; 209/164, 170; 47/1.4
See application file for complete search history.

(56) References Cited

U.S. PATENT DOCUMENTS 3,428,175 A * 2/1969 Hukki ........................... 209/164
(Continued)

FOREIGN PATENT DOCUMENTS

AU 2002101010 B4 * 5/2003
(Continued)

OTHER PUBLICATIONS

Flotation Science and Engineering, pp. 1-44 (K.A. Mattis ed., 1995) Marcel Dekker, New York, NY.

(Continued)

*Primary Examiner* — Thomas M Lithgow
(74) *Attorney, Agent, or Firm* — Phan Law Group PLLC

(57) ABSTRACT

A method of concentrating particles in a liquid-particle dispersion feed by adsorptive bubble separation by intimately contacting a gas with a pressurized stream of liquid in a chamber to form an aerated dispersion that retains at least some of the kinetic energy from the pressurized stream, and removing at least some of the kinetic energy from the aerated dispersion to form a dense foam. A liquid-particle dispersion feed is then injected into the dense foam to form a gas-liquid-particle dispersion. The gas-liquid-particle dispersion is injected into a flotation chamber at a point below a surface of a liquid contained therein, where the gas-liquid-particle dispersion forms bubbles of a gas-particle agglomerate, and the bubbles are released from the feed liquid depleted in hydrophobic particles and rise to the surface to form a floating froth enriched in particles. Also described is a device that includes plurality of chambers for aeration and mixing, feed injection, and a duct that is positioned below the liquid-foam line of a flotation chamber, so that the gas-liquid-particle dispersion is released within the chamber, and rises to the surface as a floating froth enriched in particles.

19 Claims, 4 Drawing Sheets

U.S. PATENT DOCUMENTS

| | | | |
|---|---|---|---|
| 3,802,569 | A | 4/1974 | Nagahama |
| 3,875,052 | A | 4/1975 | Lonchamp et al. |
| 3,951,805 | A | 4/1976 | Dodd |
| 4,021,303 | A | 5/1977 | Nakabayashi |
| 4,055,491 | A | 10/1977 | Porath-Furedi |
| 4,115,949 | A | 9/1978 | Avron et al. |
| 4,186,094 | A | 1/1980 | Hellberg |
| 4,288,319 | A * | 9/1981 | Heijs et al. .................... 209/166 |
| 4,425,232 | A | 1/1984 | Lawrence et al. |
| 4,554,390 | A | 11/1985 | Curtain et al. |
| 4,668,382 | A | 5/1987 | Jameson |
| 4,680,314 | A | 7/1987 | Nonomura |
| 4,800,017 | A | 1/1989 | Krishnaswamy et al. |
| 4,931,291 | A | 6/1990 | Kojima et al. |
| 4,938,865 | A | 7/1990 | Jameson |
| 4,981,582 | A | 1/1991 | Yoon et al. |
| 5,078,921 | A | 1/1992 | Zipperian |
| 5,167,798 | A | 12/1992 | Yoon et al. |
| 5,167,806 | A | 12/1992 | Wang et al. |
| 5,188,726 | A | 2/1993 | Jameson |
| 5,205,926 | A | 4/1993 | Lawrence |
| 5,240,600 | A | 8/1993 | Wang |
| 5,251,764 | A | 10/1993 | Niiti et al. |
| 5,330,913 | A | 7/1994 | Nakayama |
| 5,332,100 | A | 7/1994 | Jameson |
| 5,374,522 | A | 12/1994 | Murphy et al. |
| 5,382,358 | A | 1/1995 | Yeh |
| 5,490,924 | A | 2/1996 | Macia et al. |
| 5,626,767 | A | 5/1997 | Trampler et al. |
| 5,776,349 | A | 7/1998 | Guelcher et al. |
| 5,897,772 | A | 4/1999 | Chiang et al. |
| 5,910,254 | A | 6/1999 | Guelcher et al. |
| 5,951,875 | A | 9/1999 | Kanel |
| 6,000,551 | A | 12/1999 | Kanel et al. |
| 6,080,320 | A | 6/2000 | von Phul |
| 6,092,667 | A | 7/2000 | Steinmuller et al. |
| 6,328,165 | B1 | 12/2001 | Baker et al. |
| 6,332,980 | B1 | 12/2001 | Moorehead |
| 6,405,948 | B1 | 6/2002 | Hahn et al. |
| 6,524,486 | B2 | 2/2003 | Borodyanski |
| 6,589,785 | B1 | 7/2003 | Mullner et al. |
| 6,832,690 | B2 | 12/2004 | Kujawa |
| 2003/0201232 | A1 | 10/2003 | Cheyne |
| 2006/0084165 | A1 | 4/2006 | Lee et al. |

FOREIGN PATENT DOCUMENTS

| | | |
|---|---|---|
| DE | 3101221 | 8/1982 |
| DE | 3634903 | 4/1988 |
| GB | 2114469 | 8/1983 |
| WO | WO 92/03218 A1 * | 3/1992 |
| WO | WO 92/03219 A1 * | 3/1992 |
| WO | 2006056018 | 6/2006 |

OTHER PUBLICATIONS

Adsorptive Bubble Separation Techniques, pp. 1-5 (R. Lemlich ed., 1972) Academic Press, New York, NY.

G.V. Levin et al., "Harvesting of Algae by Froth Flotation," Applied and Environmental Microbiology, vol. 10, pp. 169-175 (1962).

Y. Christi, "Biodiesel from Microalgae," Biotechnology Advances, vol. 25, pp. 294-306 (2007).

"A Look Back at the U.S. Department of Energy's Aquatic Species Program: Biodiesel from Algae," NREL/TP-580-24190, pp. 1-294 (1998).

Olaizola, M., "Commercial Development of Microalgal Biotechnology: From the Test Tube to the Marketplace," Biomolecular Eng., Elsevier, New York, NY, vol. 20, No. 4-6, pp. 459-466 (Jul. 1, 2003).

Molina, Grima E., et al., "Recovery of Microalgal Biomass and Metabolites: Process Options and Economics," Biotechnology Advances, Elsevier Publishing, Barking, GB, vol. 20, No. 7-8, pp. 491-515 (Jan. 1, 2003).

* cited by examiner

PROCESS AND APPARATUS FOR ADSORPTIVE BUBBLE SEPARATION USING A DENSE FOAM

REFERENCE TO RELATED APPLICATION

This application claims priority under 35 U.S.C. §119(e) to U.S. Provisional Patent application 60/944,813, filed on Jun. 19, 2007, the contents of the entirety of which are incorporated herein by this reference.

BACKGROUND

Adsorptive bubble separation (which includes froth flotation, bubble fractionation, dissolved air flotation and solvent sublation) is a process in which a molecular, colloidal or particulate material is selectively adsorbed to the surface of gas bubbles that rise through a liquid, and is thereby concentrated or separated. A commonly used type of adsorptive bubble separation process is froth flotation wherein bubble-particle agglomerates accumulate on the liquid surface as a floating froth. The froth with adsorbed (i.e., attached or collected) particles is treated in one of several ways to collapse the froth and isolate the particles. See, for example, *Flotation Science and Engineering*, K. A. Mattis, Editor, pages 1-44, Marcel Dekker, New York, N.Y., 1995; and *Adsorptive Bubble Separation Techniques*, Robert Lemlich, Editor, pages 1-5, Academic Press, New York, N.Y., 1972.

This important process is commercially utilized in a wide range of applications including: isolation of minerals and metals from an ore-water slurry, dewatering of microalgae, yeast or bacterial cells, removal of oil from water, removal of ash from coal, removal of particles in waste-water treatment streams, purification of drinking water, and removal of ink and adhesives during paper recycling. In many applications, it is necessary to add reagents, known as "collectors", which selectively render one or more of the species of particles in the feed hydrophobic, thereby assisting in the process of collection by the gas bubbles. Also, frothing agents may be added to assist in the formation of a stable froth on the surface of the liquid. The process of admitting these various reagents to the system is known as conditioning.

In biochemical process engineering, adsorptive bubble separation finds utility in isolation or concentration of valuable natural products such as are produced by, for example, microalgae. Often in such applications the desired organism or biochemical product is present in very low concentrations. In such cases it is necessary therefore to feed large volumes of a very dilute aqueous dispersion of the desired material through an adsorptive bubble separation process. See, e.g., "Harvesting of Algae by Froth Flotation," G. V. Levin, et al., Applied and Environmental Microbiology, volume 10, pages 169-175 (1962). U.S. Pat. Nos. 5,776,349 and 5,951,875, the contents of each of which are incorporated herein by this reference, disclose the use of a Jameson cell for dewatering an aqueous dispersion of ruptured microalgae cells.

The particle feed for the adsorptive bubble separation process may be a mixture, dispersion, emulsion, slurry, or suspension of a molecular, colloidal and/or particulate material in a carrier liquid and is referred to hereafter as the liquid-particle dispersion feed. When the liquid is water, as is usually the case, the feed may be referred to as an aqueous-particle dispersion.

One element of the adsorptive bubble processes is the generation of bubbles, typically done by the introduction of a gas into a liquid. The efficiency of an adsorptive bubble process depends on the bubble surface area available for contact with the hydrophobic particles. Small bubbles (of a foam) have a greater surface area available for contact with hydrophobic particles than larger bubbles for a given volume of gas. However, bubbles that are too small will not rise within the carrier liquid until they coalesce, which takes time. Thus, a balance exists between the size of the bubbles and the size of the separation zone required to give the time needed for the bubbles to rise within the carrier liquid. Bubbles from 0.5 to 2 millimeters have been shown to work well within the art, although the characteristics of the carrier liquid and the hydrophobic particles can influence the design. Consistently generating bubbles of the optimum size and in sufficient quantity has been a challenging area of continued study, and many methods have been proposed and tested.

Having generated the bubbles, the hydrophobic particles are brought into contact with them with sufficient probability and energy that the hydrophobic particles penetrate the liquid boundary layer surrounding the bubbles and attach to the bubble surface. A dense bubble population results in thin films of the carrier liquid between the bubbles and greater opportunity for interaction and collection. The population of bubbles within a liquid is referred to as the "void fraction", and high void fractions favor the collection of hydrophobic particles, as there are many bubbles, and the layers surrounding them become thinner and attachment easier.

Because of the importance of adsorptive bubble separation processes, there have been many attempts to improve the efficiency and selectivity of particle capture from an aqueous-particle dispersion in order to increase product yield and purity. In all of these applications, a need exists to efficiently contact particles or droplets from a liquid dispersion with a gas and then attach the hydrophobic particles to the bubbles.

Presently columnar adsorptive bubble separation process systems fall within two broad categories—(I) those where the gas and feed flow counter-currently in a columnar system, and (II) those where the gas and feed flow co-currently, as in a compact, Jameson-type cell.

In columnar systems, the collection and separation zones are combined into a single large, tall cylindrical tank or column. The liquid-particle dispersion feed is introduced near the top of the column, and the hydrophobic particles tend to settle downward. Pressurized air or aerated liquid is introduced near the bottom forming a rising bubble flow. The rising bubbles and the settling particles must collide with enough energy for the particles to penetrate the boundary layer surrounding the bubbles and attach. As this relies on the probability of collision and energy being sufficient, the columns must be quite tall to increase the time of exposure and thus the recovery. In these counter-current flow contacting devices, a long residence time is needed to facilitate sufficient bubble-particle collision probability, making the technology relatively expensive to practice.

Examples of the counter-current columnar system include the MICROCEL™ flotation column, described in U.S. Pat. Nos. 5,167,798 and 5,078,921 as well as the Chiang Column, U.S. Pat. No. 5,897,772, the contents of each of which are incorporated herein by this reference. Similar systems include mechanical flotation cells, such as those described in U.S. Pat. No. 5,205,926, the contents of which are incorporated herein by this reference, wherein a mechanical stirring mechanism within a tank agitates the carrier liquid, the hydrophobic particles, and the gas to form the bubble generation zone. The hydrophobic particles and the bubbles are mixed in the region surrounding the impeller; where the hydrophobic particles and the bubbles collide to form hydrophobic particle-bubble agglomerates. Like the standard columnar systems, these mechanical flotation cells combine the bubble generation, contacting, collection, separation, and froth zones within the same vessel, thereby compromising the efficiency of the flotation cell, requiring a number of flotation cells operated in series in order to achieve the desired efficiency. Further, columnar systems are typically quite large and therefore impractical to move and store.

Co-current systems, which are typically based upon a Jameson cell design, are compact systems wherein feed is used to generate the foam and bubbles by means of a downward plunging jet in a downcomer, with all of the feed being fed through the jet to generate the foam/bubbles. Examples of these systems include those described in U.S. Pat. Nos. 5,332,100, 4,938,865, 4,668,382, 5,776,349, 6,092,667, WO 2006/056018 A1, and WO 2006/056018 A1 (the contents of the entirety of each of which are incorporated herein by this reference). The foam/bubbles are released into the flotation chamber through a duct or similar means, where the bubbles coalesce and disengage from the liquids, and rise to the top of the chamber to form a froth. Because adsorptive bubble processes are commonly used to separate low concentrations of hydrophobic particles from a carrier fluid, large volumes of fluid must be injected through the jet in these compact systems. Therefore, a substantial amount of power is required to charge the liquid-particle dispersion feed and the gas to the adsorptive bubble process. This power input can be a dominant cost when the adsorptive bubble process is used for the recovery of dilute material with a relatively low value, such as when algae are being dewatered for the production of biofuels.

SUMMARY OF THE INVENTION

Described is a highly efficient process and compact apparatus (flotation cell) for an adsorptive bubble separation process, requires less energy, in which a dense foam is generated prior to injecting at least a portion of the liquid-particle dispersion feed containing hydrophobic materials. These materials typically include solids, liquids, or both. By the design disclosed herein, the liquid-particle dispersion feed is injected into a mixing zone, after the generation of a dense foam. The particles collide with the bubbles of the foam to form bubble-particle agglomerates. The bubble-particle agglomerates are released into the flotation chamber, and separate from the carrier liquid in a separation zone. They then rise to the surface of the liquid for collection as a particle-rich froth.

In some embodiments, the froth naturally floats toward an open central froth collection launder into which it overflows. The action of the rising bubbles pushing the froth layer toward the reduced surface area of the center squeezes (crowds) the froth, causing bubble coalescence and increased liquid drainage thereby achieving an increased concentration of collected materials.

In some embodiments the rising bubbles and falling dislodged particles are directed to the perimeter of the flotation chamber by means of a baffle, thereby causing additional squeezing of the froth as it travels a greater distance from near the perimeter of the flotation chamber towards a central launder. This baffle is beneficial even when a central launder is not used, as it reduces the range in which the bubbles rise, and in which dislodged particles from the froth fall, thereby increasing the rate of recapture/re-adsorption of the dislodged particles, resulting in better recovery than generally obtained in the prior art.

In some embodiments, the froth is pulled by a closed loop vacuum or suction down the froth drain line, by for example drawing gas from the froth collection vessel to the gas inlet for the aspiration chamber, creating reduced pressure within the chamber that draws the froth therein. These embodiments and enhancements are particularly useful with persistent froth.

As a consequence of the design, at least some of the liquid-particle dispersion feed is injected into a vertical duct under much lower pressure (typically, only what is necessary to insure flow into the chamber), after the dense foam is formed, thereby decreasing the energy requirements of the system and preserving any flocculated particles or agglomerates that pre-exist in the liquid-particle dispersion feed. This is in contrast to compact flotation processes of the prior art wherein all of the feed is injected under high pressures, to form the foam.

The improved adsorptive bubble separation design may be utilized in any compact, mechanical or Jameson-type (or similar) flotation cell by replacing current technologies that provide for the injection of the liquid-particle dispersion to generate the dense foam, with the apparatus components of the invention, or a similar apparatus performing the methods and processes of the invention.

DETAILED DESCRIPTION OF THE INVENTION

Figure 1:
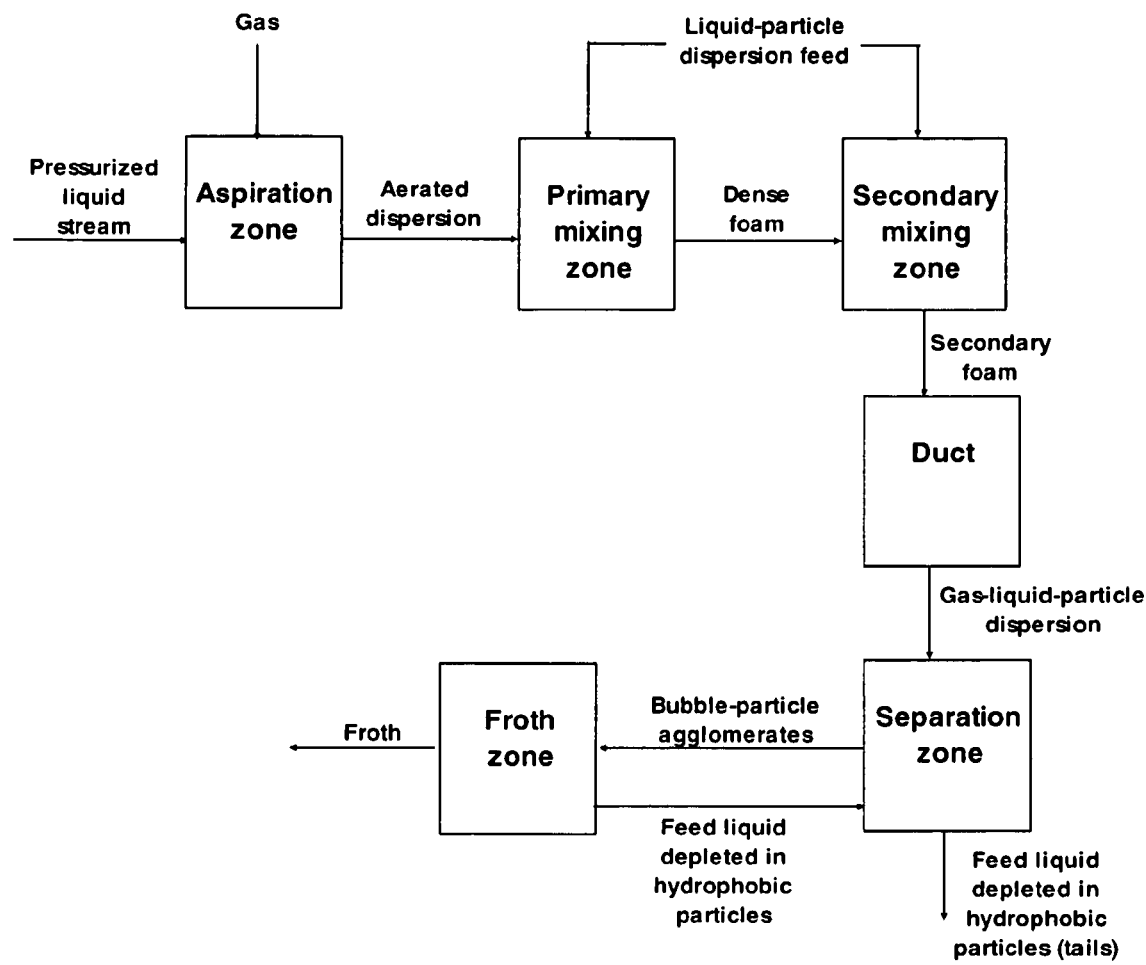
FIG. 1 is schematic block diagram of the process.

As shown in FIG. 1, the adsorptive bubble separation method includes an aspiration zone, a primary mixing zone, a secondary mixing zone, a duct, a separation zone, and a froth zone. The pressurized liquid stream (or plurality of streams) and gas enter the aspiration zone producing an aerated dispersion. The kinetic energy of the aerated dispersion is dissipated in the primary mixing zone, producing a dense foam of fine bubbles. It is desirable to produce a large number of small bubbles within the dense foam to maximize the surface area of gas available for collision with hydrophobic particles in a given volume of the liquid-particle dispersion feed.

The liquid-particle dispersion feed enters the froth flotation device in the primary and/or the secondary mixing zone, wherein the hydrophobic particles are mixed with the fine bubbles of the dense foam in an intimate manner and with enough energy to promote contact to produce a secondary foam comprising a mixture of the foam and the liquid-particle dispersion feed. The duct then allows the bubbles to further collide with the hydrophobic particles and form the gas-liquid-particle dispersion. It is desirable to generate sufficient contact in the mixing zones and the duct through fine distribution of the particles throughout the foam and high void fraction to cause a high frequency of collisions in order to achieve high particle capture efficiency.

After the bubble-particle agglomerates are formed into the gas-liquid-particle dispersion in the duct, they are then separated from the feed liquid depleted in hydrophobic particles in the separation zone, typically by gravity. The density of the gas is generally at least two to three orders of magnitude less than that of the liquid. The density difference promotes floating of the bubble-particle agglomerates to the surface of the liquid (during which process the feed liquid depleted in hydrophobic particles continues to separate from the bubble-particle agglomerates), where the agglomerates accumulate as froth in the froth zone.

Figure 3:
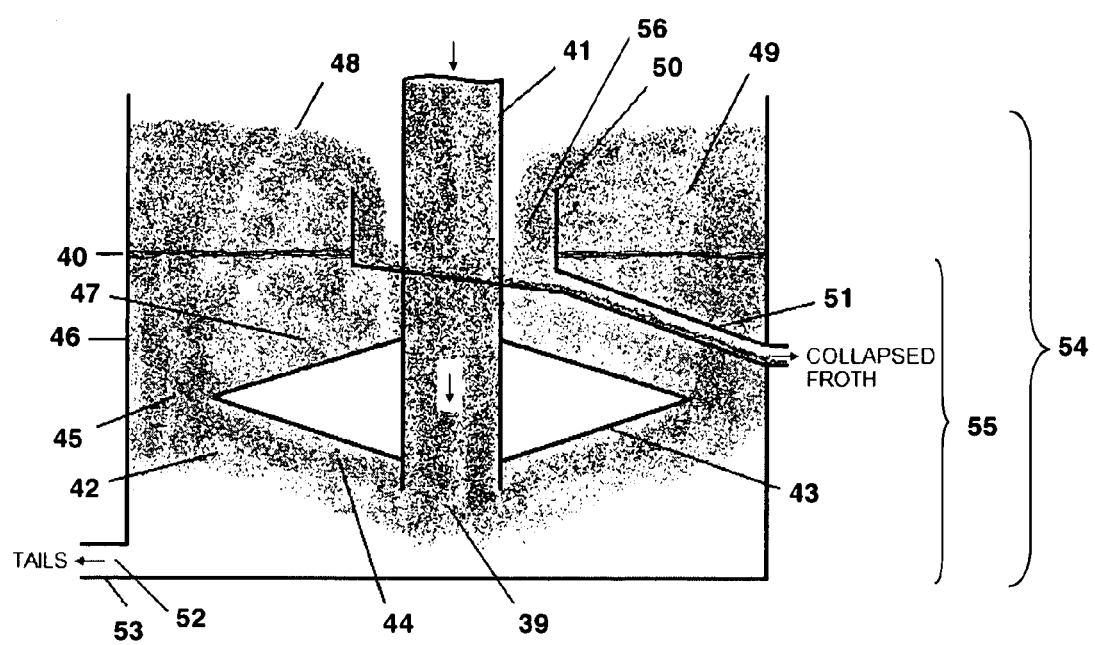
FIG. 3 is a sectional view of a portion of a cylindrical separation apparatus including the duct (sometimes termed the downcomer), a flotation chamber, a central launder and a baffle.

The froth, enriched in hydrophobic particles, overflows the froth zone as a particle-rich stream into the froth collection launder (see, e.g., 50 of FIG. 3). The underflow stream (tails), which is the feed liquid depleted in hydrophobic particles, exits the froth flotation device and may be treated again in a secondary flotation cell, recycled or discarded.

Figure 2:
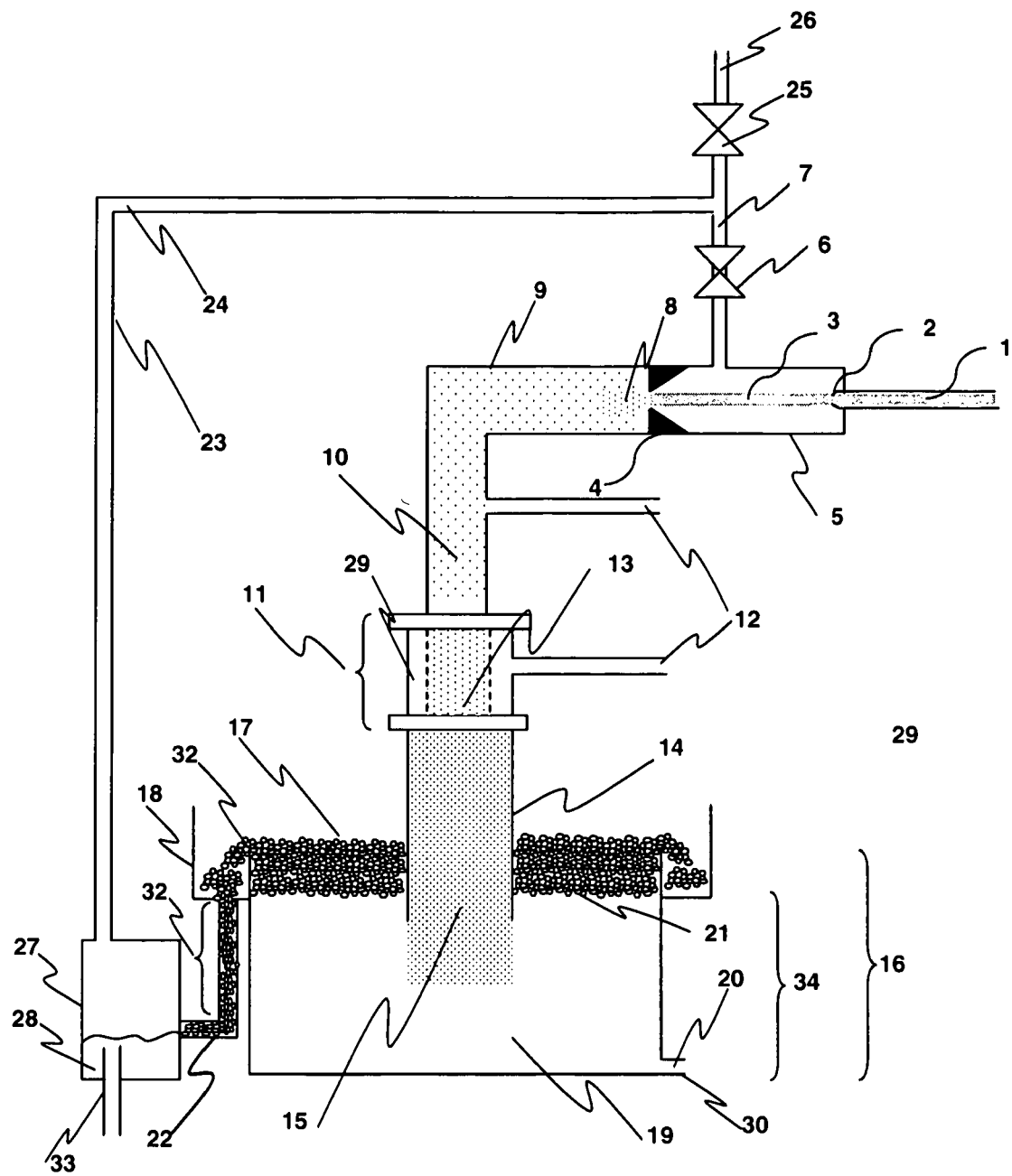
FIG. 2 is a sectional view of a cylindrical separation apparatus in which at least a portion of the liquid-particle dispersion feed is injected in one or more mixing chambers.

FIG. 2 shows a preferred apparatus for adsorptive bubble separation wherein a pressurized liquid stream 1 is injected as a free jet 3 into the aspiration chamber 5 by means of a pressurized feed nozzle 2. The nozzle may be of any shape or type capable of producing a solid or hollow liquid jet having any cross-sectional shape, or even a cone; provided, however, that preferably the nozzle is designed and configured within the apparatus to produce a jet that does not impinge against the walls of the aspiration chamber 5 or the aspiration nozzle 4, if any. The pressure of the pressurized feed nozzle can be generated by a pump or any other method capable of generating a pressurized liquid (not shown in FIG. 2). Examples of suitable pumps are known to those of skill in the art and include centrifugal, gear, peristaltic, piston, and diaphragm pumps, as well as combinations thereof.

The flow of the free jet 3 pulls gas 7 into the aspiration chamber 5, through the gas stream restriction 6. Thus, the pressure should generate a free jet having sufficient velocity to entrain gas into the free jet to form an aerated dispersion 8 as the free jet and gas exit the aspiration chamber 5. Preferably, the free jet velocity is greater than 30 feet per second, but the velocity will be dictated by the characteristics of the aerated dispersion. Thus, if the composition of the aerated dispersion is such that it is capable of sustaining stable froths, lower velocities are possible. Increasing jet velocity for a given volume imparts more energy to the aerated dispersion and can generate froths in liquids not amenable to stable froths without the addition of chemical agents. Because liquid-particle dispersion feed is added subsequently in the process, increasing the gas-liquid ratio of the aerated dispersion is sustainable within the system, as additional liquids will be available to support the bubbles of the dense foam.

The pressurized liquid stream may comprise a portion of the liquid-particle dispersion feed. It may also comprise solvents when the process is being used for liquid extraction or solvent sublation. Suitable solvents for extraction or solvent sublation include, but are not limited to, hydrocarbons, organic acids, alcohols, aldehydes, amines, esters, ethers, halogenated hydrocarbons, ketones, and any combination thereof.

Furthermore, the gas pulled into the aspiration chamber 5 may comprise air, nitrogen, argon, helium, carbon dioxide, gas from the combustion of carbonaceous material, solvent vapor, carbon dioxide from a gasification plant, or combinations thereof. In addition, reagents may be added to the gas to assist in froth generation (thereby lowering velocity requirements for the jet stream, and reducing power requirements for the system). The gas stream restriction 6 maintains a vacuum within the aspiration chamber 5 and controls the flowrate of the gas to the chamber. A higher vacuum within the aspiration chamber 5, and thus the primary mixing chamber 9, generates smaller bubbles in the dense foam 10 (thereby resulting in greater surface area for particles to adhere). Furthermore, the required pressure to generate the free jet 3 is dependant on the pressure within the aspiration chamber 5, in accordance with Bernoulli's principle.

Thus, a self-aspirating system is created, and a compressor or blower is unnecessary to form the dense foam 10 (significantly reducing the capital and operating costs of the device, and allowing for robust gas introduction without plugging problems or mechanical failures). The gas stream restriction 6 may be fixed, adjustable, or automatically variable, and may be a valve (for example, a gate valve, globe valve, or ball valve) or any other restrictions capable of controlling the passage of a gas 7 and creating a resistance to flow, including orifices and constrictions in the gas line.

An aspiration nozzle 4 may be incorporated between the aspiration chamber 5 and the primary mixing chamber 9 to stop potential flow-back from the primary mixing chamber to the aspiration chamber, and to facilitate entrainment of additional gas into the aerated dispersion 8. If more than one jet is used, then preferably there are corresponding aspiration nozzles 4 aligned with each jet. Alternatively, if more than one jet is used, the aspiration nozzle must accommodate the whole jet pattern. The aspiration nozzles 4 may be any shape in cross-section, including circular, oval, or rectangular, and may be tapering, curved, sharp edged, or otherwise.

The kinetic energy of the aerated dispersion 8 is dissipated in the primary mixing chamber 9 as it impinges upon the elbow of the primary mixing chamber, to form a dense foam 10. Kinetic energy may also be dissipated from the aerated dispersion 8 when the dispersion encounters a resistance to flow within the primary mixing chamber 9 such that it impinges upon itself, baffles, a wall, mesh or screen, structured packing or other stationary objects, or combinations thereof. Other means to dissipate the kinetic energy of the aerated dispersion 8 and create the dense foam 10 may also be used. The pressure within the primary mixing chamber 9 is less than atmospheric due to the vacuum created in the aspiration chamber 5, and thus, part of the dense foam 10 can be retained within the primary mixing chamber 9 as some passes on to the secondary mixing chamber 11. If it is desired to increase the residence time of the dense foam (for example, when very small particles are being collected by the bubbles) within the primary mixing chamber, the volume of the chamber can be increased.

Once produced, the dense foam 10 passes to the secondary mixing chamber 11, where liquid-particle dispersion feed 12 is introduced and distributed into the dense foam. As shown in FIG. 2, the liquid-particle dispersion feed 12 may also be injected into the primary mixing chamber 9. The pressure used to inject the liquid-particle dispersion feed 12 into the mixing chambers 9, 11 is preferably only that necessary to insure the flow into the chamber, and is preferably much less than the pressurized liquid stream 1 entering the aspiration chamber 5, thereby reducing the amount of energy required to introduce the liquid-particle dispersion feed 12 into the adsorptive bubble separation apparatus and also preserving any "flocs" or agglomerates that pre-exist in the liquid-particle dispersion feed. In certain applications where the pressurized liquid forms very stable and fine bubble froths, such as some oil-water dispersions, lower pressure of the pressurized liquid should be used, as the whole separation vessel may fill with foam without forming a defined froth-liquid interface for froth separation. In such cases, very little energy is required to generate the aerated dispersion, and the pressure of the pressurized liquid may be as low as about 5 psi.

The liquid-particle dispersion feed 12 may be introduced into the mixing chambers 9, 11 through nozzles, feed distributors, mesh pads, diffusers, a porous media, or combinations thereof. The pressure that the liquid-particle dispersion feed enters the mixing chambers will be less than that which the pressurized liquid enters the aspiration chamber. Alternatively, as shown in FIG. 2, the liquid-particle dispersion feed 12 may be injected into a chamber 29 annular to the mixing chamber, where the separating wall between the two chambers has a plurality of orifices or other means to allow the liquid-particle dispersion feed to be introduced into the mixing chamber with enough energy to facilitate intimate and relatively quiescent contact of the bubbles of the dense foam 10 and the liquid-particle dispersion feed 12. The mixing chambers 9, 11 may contain plates, tubes, pipes or any other system to distribute the liquid-particle dispersion feed throughout the dense foam. These plates, tubes or pipes may be perforated, of different length, or they may be moving such that the liquid-particle dispersion feed is distributed within the dense foam. Preferably, the introduction and mixing components, if any, do not plug or significantly increase the pressure requirement of the liquid-particle dispersion feed introduction, and by design distribute the liquid-particle dispersion feed throughout the dense foam.

From the secondary mixing chamber 11, the secondary foam 13 passes into a duct 14, where the hydrophobic particles of the liquid-particle dispersion feed continue to be captured by the bubbles of the foam and become the gas-liquid-particle dispersion 15. The bottom of the duct 14 is submerged below the liquid surface (froth-liquid interface) 21 of the flotation chamber 16. The duct 14 may be vertical, have a vertical section, or be angled from vertical so that it contains the column of foam in a manner so that sufficient vacuum is maintained in the mixing chambers 9, 11 and the duct 14 to maintain a column of at least some of the gas-liquid-particle dispersion 15 in the duct, and to maintain the requisite vacuum in the aspiration chamber 5.

The gas-liquid-particle dispersion 15 is introduced into the separation zone 34 within the flotation chamber 16, where it begins to coalesce into larger bubbles, disengage from the feed liquid depleted in hydrophobic particles, and rise toward the liquid surface 21 carrying the collected materials. The separation zone 34 can be configured in any shape so long as the residence time is sufficiently great to allow for bubble coalescence and the separation of the bubble-particle agglomerates and the feed liquid depleted in hydrophobic particles 20. Even though the separation zone 34 may be cylindrical, square, rectangular, hexagonal, or other shape, it is preferable to use a cylindrical design.

The rising bubble-particle agglomerates accumulate as froth 17 above the liquid surface (froth-liquid interface) 21 in the froth zone. In this zone, the froth continues to drain, purifying the froth and concentrating the collected material. As additional bubbles rise forming more froth, the bubbles push the accumulated froth onto the surface toward the launder lip 31; the upper portion of the froth overflows the launder lip 31 into the froth collection launder 18. FIG. 2 shows a perimeter launder; FIG. 3 shows a new configuration for the separation zone and froth collection launder suitable for use with aspiration and mixing chambers previously described, wherein the launder is centrally located within the flotation chamber 16 so that the accumulated froth is pushed toward a reduced surface area. This movement toward the reduced surface area of the center squeezes the froth, helping to cleanse and drain it.

Wash liquid may be added to the froth from above if desired to further purify it. Any suitable liquid can be used for the froth washing operation. Suitable liquids include, but are not limited to water, liquids that are native to the liquid-particle dispersion feed, solutions of surface treatment and conditioning agents, and combinations thereof.

The froth and collapsed froth 22 drain down the froth collection launder 18 and then exit the flotation chamber 16 through the bottom or the side via a froth drain line 32. The feed liquid depleted in hydrophobic particles (tails) 20 underflows the flotation device through a bottom or side tails line 30 and may be treated again in a secondary flotation cell, recycled or discarded. The liquid level in the flotation chamber 16 may be maintained by controlling the flow of the feed liquid depleted in hydrophobic particles 20 though the tails discharge by any method known in the art, including but not limited to a valve, an orifice, or a swing-arm. The bottom of the flotation chamber 16 may be flat, hemispherical or conical. In processes in which solids settle to the bottom, a sloped-flat, hemispherical or conical bottom with bottom tails line 30 is desired for improved solids removal.

The aspiration chamber 5, mixing chambers 9, 11 and duct 14 can be cylindrical, spherical, rectangular, or any shape or combination of shapes. Similarly, the collection launder 18 may be annular or partially annular to the outer wall of the flotation chamber, or may be any shape within the flotation chamber 16; when within the flotation chamber, the collection launder preferably forms an annulus around the duct 14. They may be constructed of any material used in the art, including but not limited to polyvinyl chloride (PVC), high-density polyethylene (HDPE), polycarbonate, other polymers, glass, fiberglass, ceramic, steel, iron, other metals, concrete, tile, or other construction materials. Preferably, they are constructed of materials compatible with the aerated dispersion and the liquid-particle dispersion feed and resistant to erosion or corrosion. Further, they may be constructed as independent units, or as a combined unit.

The outer wall of the flotation chamber may be constructed from any material used in the art, including but not limited to PVC, HDPE, polycarbonate, other polymers, glass, fiberglass, steel, iron, other metals, concrete, tile, earth, stone, or other construction materials.

Although the described embodiment shows a method to produce dense foam, other means to produce the foam known may be used, such as aspiration of the gas into a liquid using an eductor, a plunging jet, or an agitated system. Further, the liquid-particle dispersion feed may be injected into the primary mixing chamber in addition to or in lieu of the addition into the secondary mixing chamber, preferably at a reduced pressure. When the hydrophobic particles are hard to capture, such as when they are very small in size or are not extremely hydrophobic, the energy of the high velocity jet in the area of insertion of the liquid-particle dispersion feed can be used to promote contact of the bubbles and hydrophobic particles that may lead to the formation bubble-particle agglomerates in the primary mixing chamber.

Also depicted in FIG. 2 is an optional, novel method using a partial vacuum (downdraft) to pull the froth and collapsed froth through the froth collection launder 18 and froth drain line 32 into a froth accumulator 27. This method greatly assists froth collection (especially persistent froths) as the froth can be pulled by suction through the discharge system more easily than it can be drained by gravity or pushed through the line. This partial vacuum or suction can be generated by any method known in the art for creating a vacuum/suction, but it is particularly useful if the gas 7 used to generate the aerated dispersion is pulled through the froth drain line 32, through the froth accumulator 27 and into the aspiration chamber. Preferably, the vacuum is generated by a closed loop design, wherein the froth and collapsed froth exit the drain line into the froth accumulator 27. The froth accumulator 27 is connected to the gas inlet for the aspiration chamber 5, so that as the force of the jet draws gas 7 into the aspiration chamber 5, gas 24 is pulled from the froth accumulator 27 via gas line 23. To control the vacuum pressure, an additional valve 25 is placed on the source gas line 26, thereby controlling the amount and make-up of the gas 7 injected into the aspiration chamber 5. The collapsed froth leaves the froth accumulator 27 through the collapsed froth exit line 33.

FIG. 3 shows a partial view of an apparatus for adsorptive bubble separation, with optional elements including a central launder 50 and baffles 43 incorporated into the design. The aspiration chamber and mixing chambers discussed above are not shown but are intended to be a part of this apparatus.

In this embodiment, the secondary foam passes from the secondary mixing chamber into the duct 41, where the hydrophobic particles of the liquid-particle dispersion feed continue to be captured by the bubbles of the foam and become the gas-liquid-particle dispersion 39. The gas-liquid-particle dispersion is introduced below the liquid surface (froth-liquid interface) 40 of the flotation chamber 54 from the duct 41 into the separation zone 55 of the flotation chamber 54. The duct 41 introducing the gas-liquid-particle dispersion may be vertical, have a vertical section, or be angled from vertical so that it contains the column of foam in a manner so that sufficient vacuum is maintained in the chambers and duct to maintain a column of at least some of the gas-liquid-particle dispersion in the duct, and to maintain the requisite vacuum in the aspiration chamber.

The bottom of the duct 41 is submerged below the liquid surface 40 within the separation zone 55 where the exiting gas-liquid-particle dispersion 39 begins to coalesce into larger bubbles 42, disengage from the carrying liquid, and rise toward the liquid surface carrying the collected materials. The separation zone can be configured in any shape so long as the residence time is sufficiently great to allow for bubble coalescence and the separation of the bubble-particle agglomerates and the feed liquid depleted in hydrophobic particles.

The froth baffle 43 directs the bubbles 44 outward to the gap 45 between the baffle 43 and the perimeter wall 46 of the separation zone where they then rise toward the froth-liquid interface 40. Likewise disengaged particles 47 that are sinking are directed outward by the baffle 43 to the gap 45 where they will be re-contacted with rising bubbles 42. The froth baffle may be of any shape that directs the rising bubbles and the sinking particles to a location near the perimeter. The baffle may be conical, flat, tapered, or sloped and constructed from any material used in the art, including but not limited to PVC, HDPE, polycarbonate, rubber, other polymers, glass, fiberglass, steel, iron, other metals, concrete, tile, or other construction materials. The baffle may be wedge shaped.

The rising bubble-particle agglomerates accumulate as froth 48 above the froth-liquid interface 40 in the froth zone 49. In this zone, the froth continues to drain, purifying the froth and concentrating the collected material. As additional bubbles rise forming more froth, they push the accumulated froth 48 toward the lip of the launder 50, and the upper portion of the froth overflows the lip into the froth collection launder 50. As shown in FIG. 3, the launder may be centrally located within the flotation chamber 16, so that the accumulated froth is pushed toward a reduced surface area. This movement toward the reduced surface area of the center squeezes the froth, helping to cleanse and drain the froth.

Wash water may be added to the froth 56, in the launder from above if desired to further purify it. Any suitable liquid can be used for the froth washing operation Suitable liquids include, but are not limited to water, liquids that are native to the liquid-particle dispersion feed, solutions of surface treatment and conditioning agents, and combinations thereof.

The froth and collapsed froth 56 drain down the collection launder 50 and then exit the flotation chamber through the bottom or the side via a drain line 51. The feed liquid depleted in hydrophobic particles (tails) 52 underflows the flotation device through a bottom or side tails line 53 and may be treated again in a secondary flotation cell, recycled or discarded. The liquid level 40 in the flotation chamber 54 may be maintained by controlling the flow of the feed liquid depleted in hydrophobic particles 52 though the tails line 53 by any method known in the art, including but not limited to a valve, an orifice, or a swing-arm. The bottom of the flotation chamber 54 may be flat, hemispherical or conical. In processes in which solids settle to the bottom, a sloped-flat, hemispherical or conical bottom with bottom tails line is desired for improved solids removal.

One of the design parameters in flotation cell design is $J_g$ (the superficial gas rise rate), and it is typically calculated by dividing the gas flow rate entering the cell by the cell area. High $J_g$ rates (greater than 1 cm per second) will typically produce high recovery as a rapid bubble rise rate leaves less time for the bubbles to coalesce and particles to disengage. In this rising stream, gangue and liquid can be entrained in the flow also. Lower $J_g$ rates (less than 1 centimeter per second) allow more time for bubble coalescence and drainage of the froth to produce a more pure froth. An even rise of bubbles is assumed in the calculation of $J_g$. In the prior art, it is understood that uniformity in the froth flow path results in uniform treatment of the froth and gives more predictable performance. With a central froth baffle in a cylindrical tank, froth distribution takes place in a radial direction with constant distances and a uniform inward froth flow path throughout 360 degrees.

In the described process, the liquid-particle dispersion feed comprises particles (one or more types) and a carrier fluid, usually, water. The particles may comprise solid particles, molecules, colloids, liquid droplets, or combinations thereof. Examples of the solid particles include, but are not limited to minerals, gangue, micro-organisms, coal, inks, pigments, or combinations thereof. Molecular examples might include color bodies, humic and fulvic acids, cellulose, and lignins. Colloidals might include precipitates in water (iron and calcium compounds especially), metal oxides, silt, clays, dead or living phytoplankton (and zooplankton for that matter), ligands, metal complexes, etc. Examples of liquid droplets include, but are not limited to organic solvents, metal extraction solvents, dyes, inks, oils, hydrocarbons, fuels, triglycerides, carotenoids, natural products, biodiesel, or other fluids that are above their melting point and below their boiling point at the system pressure and temperature.

Practical examples of the liquid-particle dispersion feeds requiring separation include but are not limited to minerals and gangue, aqueous dispersions of micro-organisms (microalgae, bacteria, fungi, and/or viruses), aqueous dispersions of oil droplets and unwanted particulates, aqueous dispersions of triglycerides, coal and unwanted materials (e.g., ash), particles in waste-water treatment streams, and inks and/or adhesives on paper for recycling, or combinations thereof. Micro-organisms in the feed may be alive and/or dead, whole and/or ruptured. The apparatus and process of this invention is especially useful for the concentration (dewatering) of ruptured microalgal cells and microalgal cellular components in water. Additives may be introduced to facilitate flotation of micro-organism cells such as alum, ferric chloride, poly-electrolytes, polymers, and other flocculants known in the art. The carrying liquid may be water, brine, seawater, aqueous solutions, growing media for the microalgae or reagents or a combination of any of these.

Any species of microalgae may be separated from a carrier liquid by means of the process or apparatus of the invention. These species include, but are not limited to *Anabaena, Anki-* strodesmus falcatus, Arthrospira (Spirulina) obliquus, Arthrospira (Spirulina) platensis, Botryococcus braunii, Chaetoceros gracilis, Chlamydomonas reinhardtii, Chlorella vulgaris, Chlorella pyrenoidosa, Chlorococcum littorale, Cyclotella cryptica, Dunaliella bardawil, Dunaliella salina, Dunaliella tertiolecta, Dunaliella viridis, Euglena gracilis, Haematococcus pluvialis, Isochrysis galbana, Nannochloris, Nannochloropsis salina, Navicula saprophila, Neochloris oleoabundans, Nitzschia laevis, Nitzschia alba, Nitzschia communis, Nitzschia paleacea, Nitzschia closterium, Nostoc commune, Nostoc flagellafonne, Pleurochrysis carterae, Porphyridium cruentum, Prymnesium, Pseudochoricystis ellipsoidea, Scenedesmus obliquus, Scenedesmus quadricauda, Scenedesmus acutus, Scenedesmus dimorphus, Skeletonema costatum, Spirogyra, Spirulina, Synechoccus, Amphora, Fragilaria, Schizochytrium, Rhodomonas, and genetically-engineered varieties of these microalgal species. It should be understood that an additional reason for the separation of microalgae may be to clean the carrying liquid, rather than just for the purpose of concentrating microalgal biomass.

Microalgae cells may be ruptured by any method known in the art including the method described by Kanel in U.S. Pat. No. 6,000,551 (the contents of the entirety of which is incorporated herein by this reference) and by intimately contacting the microalgae and the grinding media in a grinding apparatus. Suitable grinding apparati include vibratory grinding mills, agitated bead mills (stirred media mill) or a sonication chamber containing grinding media.

Further, harmful algal blooms (blooms of toxic algae also termed HABs) may be remediated by removal from seawater using the process or apparatus of the invention. The HABs term is used to describe a toxic bloom whether the alga is red (e.g., "red tide"), yellow, golden, brown, or blue-green. HABs have been associated with blooms of Rhodophytes, Chysophytes, and Synurophytes, etc. The best known HAB agent is a cyanobacterium, *Microcystis aeruginosa*, a freshwater blue-green alga. But other blue-greens include *Anabaena*, *Aphanizomenon*, and *Cylindrospermopsis*. *Karenia brevis* is the HAB prevalent off of the coasts of Florida, North Carolina, Alabama, Mississippi, Louisiana, and Texas. In New England, the toxic dinoflagellate *Alexandrium* has been troublesome along the coastline. The heterotrophic dinoflagellate, *Protoperidinium crassipes*, has been implicated in some recent HABs. Some farm fisheries have been plagued by a raphidophyte, *Heterosigma akashiwo*.

In mineral processing applications, the liquid-particle dispersion feed is typically conditioned using surface chemistry treatments as are known in the art to render the desired mineral hydrophobic. The described methods and apparatus are also useful in those instances where the undesired material is rendered hydrophobic and is removed with the froth. In such cases, the underflow contains the desired material.

Due to the difficulty in transporting froths in ducts and pipes, it is preferable to collapse the purified froth in the collection launder. The purified froth that overflows into the collection launder naturally collapses or is treated in one of several known ways to collapse the froth and isolate the concentrated material. With more persistent froths, more aggressive action must be taken to collapse them. Sprays in the froth collection launder may be used. The liquid used for the sprays can be water or any other liquid. So as to not dilute the collected material, the liquid portion of the collapsed froth can be recirculated through the spray nozzles. The spray nozzles may be of a design to prevent clogging. Air or gas selected from those used for creation of the foam can also be used to break the froth. When the froth is allowed to flow to the perimeter of the separation vessel for collection in launders, the area needing treatment is the entire perimeter of the vessel. This addition of spray liquid can be large thus diluting the froth and partially defeating the purpose of the operation. This dilution is undesirable because adsorptive bubble separation is commonly used for the concentration of a hydrophobic material. Therefore, the central collection launder is preferred, as it has a lower surface area and requires less spray volume.

Chemical methods for breaking froth include, but are not limited to, the use of chemical defoamers. These defoamer liquids can be sprayed onto the froth surface or distributed within a wetted pad that contacts the froth as it flows into the froth collection launder. These chemical methods are also applicable for use herein and the lower surface area of the central collection launder may result in the use of less chemical defoamer.

Mechanical methods to break the froth include, but are not limited to, sonication methods, vibrating or spinning objects in the froth region, etc. Also, combinations of chemical and mechanical coalescing techniques can be used to coalesce the bubbles and form a region enriched in the particles to be separated from the liquid stream. These mechanical methods are also applicable to use in the instant invention and the lower surface area of the central collection launder may use smaller and less expensive equipment.

Figure 4:
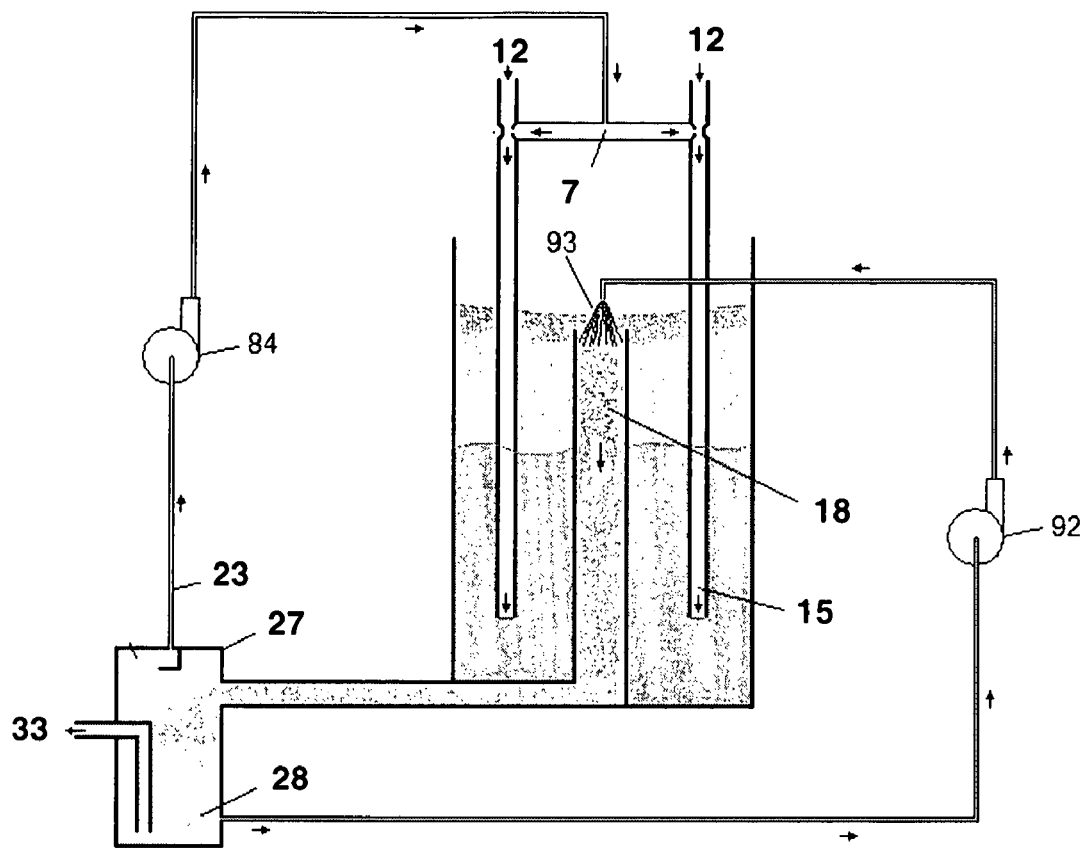
FIG. 4 is a sectional view of a spray-aided froth collection separation apparatus, wherein a spray is used to improve froth collection.

A second optional enhancement, spray-aided froth collection, illustrated in FIG. 4, may be used with or without the previous vacuum-aided froth collection. It may also be used with the central launder or with a peripheral launder. In this optional enhancement, a spray 93 is used to improve froth collection. A pump 92 is used to generate the spray from the collapsed froth liquids 28 in the froth accumulator. The spray 93 drives the persistent froth into the froth collection launder 18. The use of collapsed froth liquids for this spray prevents dilution of the collected materials. A gas pump 84 is shown here to remove gas from the froth accumulator.

In the case of particulate flotation, where the gangue material is denser than the liquid in the liquid-particle dispersion feed, a sloped bottom and a solids relief discharge will be needed to remove solids from the separation vessel. If the feed rate of the liquid-particle dispersion feed is somewhat constant, this solids relief discharge can be controlled by the use of a small valve set to discharge from the sloped bottom and remove the solids in a heavy slurry. In another aspect, this removal could be through a small solids handling pump.

The process and apparatus for adsorptive bubble separation is further described by the following illustrative Examples.

Example 1

Electrolyte Cleaning for Copper Solvent Extraction

A pilot-scale flotation cell is constructed according to the design of FIG. 2 with the liquid-particle dispersion feed having 0.1 wt % droplets of the extraction solvent entrained in the feed to an electrolyte unit. The flow rate of the pressurized liquid stream is 2 liters per minute and the jet velocity in the aspiration chamber is 20 meters per second. The pressurized liquid stream is made up of a portion of the feed liquid depleted in hydrophobic particles from the tails discharge of the separation zone. The gas is ambient air, and the gas stream restriction is a valve adjusted to maintain a flow rate of 2 liters per minute. The jet passes through the aspiration nozzle and becomes the aerated dispersion, entering the primary mixing chamber where its kinetic energy is substantially removed upon contact with the elbow of the chamber, as well as upon contact with dense foam residing in the chamber. The volume of the primary mixing chamber is 0.6 liters, and thus the residence time of this dense foam is 9 seconds. The dense foam exits the primary mixing chamber into the secondary mixing chamber, where 10 liters per minute of the liquid-particle dispersion feed is introduced. The secondary foam enters the duct where the droplets of extraction solvent are collected by the bubbles of the foam to form the gas-liquid-particle dispersion, which is subsequently discharged into the separation zone. The inside diameter of the duct is 1.96 cm, and it is 300 cm long. The residence time in the duct is 3.9 seconds. Upon exit from the duct into the separation zone, the bubbles of the gas-liquid-particle dispersion (with the collected droplets of extraction solvent thereon) coalesce and rise to the liquid surface, creating a hydrophobic particle-rich froth containing 85% of the extraction solvent fed to the unit. The hydrophobic particle-rich froth is collected in the froth collection launder. The feed liquid depleted in hydrophobic particles flows out of the separation zone and the flotation cell in a controlled fashion to maintain the liquid level within the separation zone above the discharge end of the duct.

Example 2

Solvent Recovery from Raffinate for Copper Solvent Extraction

A pilot-scale flotation cell is constructed according to the design of FIG. 2 with the flow rate of the pressurized liquid stream at 10 liters per minute and a velocity of 20 meters per second. The pressurized liquid stream is made up a portion of the liquid-particle dispersion feed containing 0.1% droplets of extractant in the aqueous phase. The pressurized liquid enters the aspiration chamber pulling gas into the stream creating an aerated dispersion. The flow rate of the gas is 5 liters per minute. The volume of the primary mixing chamber is 1.0 liters, and thus the residence time of the aerated dispersion is 4 seconds. The dense foam exits the primary mixing chamber into the secondary mixing chamber, where 15 liters per minute of the remaining liquid-particle dispersion feed is added. This liquid-particle dispersion and foam enters the duct where the droplets of extractant are collected by the bubbles of the foam and exits the duct as the gas-liquid-particle dispersion that discharges into the separation zone. The inside diameter of the duct is 2.52 cm, and it is 300 cm long. The residence time in the duct is 3 seconds. Upon exit from the duct in the separation zone, the bubbles of the gas-liquid-particle dispersion (with the collected droplets of extractant thereon) coalesce and rise to the liquid surface, forming the hydrophobic particle-rich froth. This froth is collected in the froth collection launder. The flow rate of the froth is 0.5 liters per minute and contains 4.25% by weight of the droplets of extractant. Thus, 85% of the entrained droplets are recovered in the froth and concentrated by a factor of 43. The feed liquid depleted in hydrophobic particles flows from the separation zone and the flotation cell in a controlled fashion to maintain the liquid level within the separation zone above the discharge end of the duct.

Example 3

Dewatering of an Algal Dispersion

A commercial size froth flotation cell is constructed according to the design of FIG. 2 with the flow rate of the pressurized liquid stream is 150 liters per minute and the velocity is 20 meters per second. The liquid-particle dispersion feed comprises 100 ppm *Dunaliella sauna* algae that have been ruptured. The pressurized liquid stream is made up of the feed liquid depleted in algae from the separation zone and represents a recirculation of a portion of that discharge. The flow rate of the gas is 100 liters per minute. The pressurized liquid stream passes through the aspiration nozzle into the primary mixing chamber. The volume of the primary mixing chamber is 47 liters, and thus the residence time of this mix is 11.3 seconds. The dense foam exits the primary mixing chamber into the secondary mixing chamber, where 750 liters per minute of the liquid-particle dispersion feed is added through a distribution nozzle. The liquid-particle dispersion and the foam flow through the duct where the algae are collected by the bubbles of the foam to form the gas-liquid-particle dispersion that discharges into the separation zone. The algae-rich froth is collected in the froth collection launder. The inside diameter of the duct is 20.3 cm, and it is 300 cm long. The residence time in the duct is 5.8 seconds. The flow rate of the froth is 31.9 liters per minute and contains 0.2% algal biomass. This represents a concentration factor of 20 times and a recovery of 85% of the algae in the froth.

Example 4

Mineral Recovery

The same pilot-scale flotation cell of Example 1 is used in this Example. The flow rate of the pressurized liquid stream is 4 liters per minute and the velocity is 20 meters per second. This stream consists of water with 10 ppm polypropylene glycol as a froth promoter. The flow rate of the gas is 8 liters per minute. The resulting aerated dispersion enters the primary mixing chamber through the aspiration chamber and the aspiration nozzle to form a dense foam. The volume of the primary mixing chamber is 0.6 liters, and thus the residence time of this mix is 3 seconds. The liquid-particle dispersion feed is an aqueous slurry of 25 wt % solids of the copper sulfide ore chalcocite ($Cu_2S$) particles with a mean particle size of 80 micrometers. The density of the copper sulfide ore particles is 5.5 g/ml, and the solids contain 0.1% chalcocite. The liquid-particle dispersion feed has been treated with a xanthate type of collector. The dense foam is mixed in the secondary mixing chamber with 2.5 kilograms per minute (8 liters per minute) of the liquid-particle dispersion feed, which is introduced through a distribution nozzle. This liquid-particle dispersion and foam enters the duct where the chalcocite particles are collected by the air bubbles to form the gas-liquid-particle dispersion. This gas-liquid-particle dispersion is discharged from the duct and enters the separation zone where the collected chalcocite particles rise with the bubbles for collection. The inside diameter of the duct is 3.53 cm, and it is 300 cm long. The residence time in the duct is 6 seconds. Upon entering the separation zone, the bubbles in the gas-liquid-particle dispersion coalesce and rise to the liquid surface forming a froth rich in chalcocite particles. This froth flows into the froth collection launder at the rate of 0.94 kilograms per minute containing 2 wt % chalcocite. This represents 75% recovery of the chalcocite and an upgrade of 20 times in grade.

What is claimed is:
1. A method of concentrating algal particles in a liquid-particle dispersion feed by adsorptive bubble separation, the method comprising:
    intimately contacting a gas with a pressurized stream of liquid in a chamber to form an aerated dispersion that retains at least some kinetic energy from the pressurized stream;

removing at least some of the kinetic energy from the aerated dispersion to form a dense foam;

introducing the liquid-particle dispersion feed into the dense foam, after the dense foam is formed, to form a gas-liquid-particle dispersion and thereby preserve any flocculated particles or agglomerates in the liquid-particle dispersion feed;

introducing the gas-liquid-particle dispersion into a flotation chamber at a point below a surface of a liquid concentrated therein, wherein the gas-liquid-particle dispersion in the flotation chamber forms bubbles comprising a gas-particle agglomerate, and wherein the bubbles rise to the surface of the liquid in the flotation chamber to form a floating froth enriched in the particles;

collecting the froth in a froth collection launder; and spraying collapsed froth liquid into the froth collection launder to drive persistent froth into the launder.

2. The method according to claim 1, wherein the froth collection launder is located in an area having less surface area than the region where the froth is formed.

3. The method according to claim 1, further comprising:

directing the rising bubbles to the surface of the liquid, near the perimeter of the flotation chamber, by means of one or more baffles.

4. The method according to claim 1, wherein at least some of the particles are selected from the group consisting of microalgae, ruptured microalgae, and combinations thereof.

5. The method according to claim 4, wherein the particles are of *Dunaliella salina*.

6. The method according to claim 5, further comprising:

rupturing the microalgae by intimately contacting the microalgae and grinding media in a grinding apparatus prior to introduction into the dense foam.

7. The method according to claim 1, further comprising:

directing rising bubbles and falling dislodged particles to the perimeter of the flotation chamber by a baffle.

8. The method according to claim 1, further comprising:

injecting at least a portion of the liquid-particle dispersion feed into a chamber annular to a mixing chamber, wherein the two chambers comprise a separating wall having a plurality of orifices to allow the liquid-particle dispersion feed to be introduced into the mixing chamber with enough energy to facilitate intimate and relatively quiescent contact of the bubbles of the dense foam and the liquid-particle dispersion feed.

9. In an adsorptive bubble separation process of the type involving froth flotation on a liquid surface flowing into a froth collection launder, wherein the improvement comprises:

providing a dense foam flowing towards a flotation chamber;

injecting a liquid-particle dispersion feed into the dense foam, after the dense foam is formed, to preserve any flocculated particles or agglomerates in the liquid-particle dispersion feed; and spraying collapsed froth liquid into the froth collection launder to drive persistent froth into the launder.

10. An apparatus for concentrating algal particles in a liquid-particle dispersion by adsorptive bubble separation, the apparatus comprising:

a flotation chamber having a perimeter wall, and designed to hold liquid;

a first structure for generating an aerated dispersion, the first structure comprising:

an aspiration chamber, means for pressurizing a stream of liquid and injecting the pressurized stream of liquid into the aspiration chamber, and means for providing and controlling the delivery of a gas from a gas inlet into the aspiration chamber, wherein the gas and pressurized stream of liquid form an aerated dispersion having kinetic energy;

a second structure for generating a dense foam of bubbles from the aerated dispersion, said second structure comprising a first mixing chamber configured to receive the aerated dispersion and remove at least some kinetic energy from the aerated dispersion;

means for introducing the liquid-particle dispersion into the dense foam after at least some of the kinetic energy has been removed from the aerated dispersion to preserve any flocculated particles or agglomerates in the liquid-particle dispersion;

a duct configured to allow the particles in the liquid-particle dispersion to adsorb onto the bubbles of the dense foam, wherein the duct is positioned within the flotation chamber, having an opening below the liquid surface within the flotation chamber;

a froth collection launder having a discharge line for collecting froth from the flotation chamber; and a spray for spraying collapsed froth liquid into the froth collection launder to drive persistent froth into the launder.

11. The apparatus of claim 10, wherein the froth collection launder is located substantially centrally to the perimeter wall of the flotation chamber, and wherein a horizontal edge of the froth collection launder is below a horizontal edge of a perimeter wall of the flotation chamber.

12. The apparatus of claim 11, further comprising:

a baffle attached to an outer side of the froth collection launder, wherein the baffle prevents liquid flowing at a vertical interface between the baffle and the froth collection launder.

13. The apparatus of claim 11, further comprising means for creating a vacuum in the discharge line of the froth collection launder.

14. The apparatus of claim 13, wherein the means for creating a vacuum comprises a closed loop design between the collection launder and the gas inlet.

15. The apparatus of claim 10, wherein at least some of the particles are selected from the group consisting of microalgae, ruptured microalgae, and combinations thereof.

16. The apparatus of claim 15, wherein the particles are of *Dunaliella salina*.

17. The apparatus of claim 16, further comprising:

a grinding apparatus for rupturing the microalgae prior to introduction into the dense foam by intimately contacting the microalgae and grinding media in the grinding apparatus.

18. The apparatus of claim 10, further comprising:

a baffle in the flotation chamber for directing rising bubbles and falling dislodged particles to the perimeter of the flotation chamber.

19. The apparatus of claim 10, further comprising:

a chamber annular to the mixing chamber for injecting at least a portion of the liquid-particle dispersion feed into the mixing chamber, wherein the two chambers comprise a separating wall having a plurality of orifices to allow the liquid-particle dispersion feed to be introduced into the mixing chamber with enough energy to facilitate intimate and relatively quiescent contact of the bubbles of the dense foam and the liquid-particle dispersion feed.

* * * * *